United States Patent [19]

Kaye

[11] Patent Number: 4,590,037

[45] Date of Patent: May 20, 1986

[54] MEANS FOR CONSECUTIVE INTRODUCTION OF CO-ACTING STERILANTS INTO A STERILIZING CHAMBER

[75] Inventor: Saul Kaye, Evanston, Ill.

[73] Assignee: Ben Venue Laboratories, Inc., Bedford, Ohio

[21] Appl. No.: 707,578

[22] Filed: Mar. 4, 1985

Related U.S. Application Data

[63] Continuation-in-part of Ser. No. 492,709, May 9, 1983, which is a continuation-in-part of Ser. No. 212,973, Feb. 13, 1981, abandoned.

[51] Int. Cl.⁴ .............................................. A61L 2/20
[52] U.S. Cl. ..................................... 422/116; 222/83; 222/85
[58] Field of Search ................... 222/81, 83, 83.5, 85, 222/86, 160; 414/403, 404, 412; 422/27, 28, 34, 116, 237

[56] References Cited

U.S. PATENT DOCUMENTS

| | | | |
|---|---|---|---|
| 3,068,064 | 12/1962 | McDonald | 422/34 |
| 3,987,791 | 10/1976 | Chittenden et al. | 222/83 |
| 4,066,399 | 1/1978 | Gunther | 422/27 |
| 4,081,006 | 3/1978 | Crowell et al. | 222/83.5 |

Primary Examiner—Ivars Cintins
Attorney, Agent, or Firm—Robert Bruce Henn

[57] ABSTRACT

Contiguous puncturable containers of water and ethylene oxide are provided as a unitary device to provide successive introduction and vaporization into a chamber in which there are contained objects to be sterilized. The containers comprising the unitary structure are opened in succession to provide necessary humidity followed by the introduction of ethylene oxide gas, where both substances are necessary for accomplishing effective sterilization.

4 Claims, 5 Drawing Figures

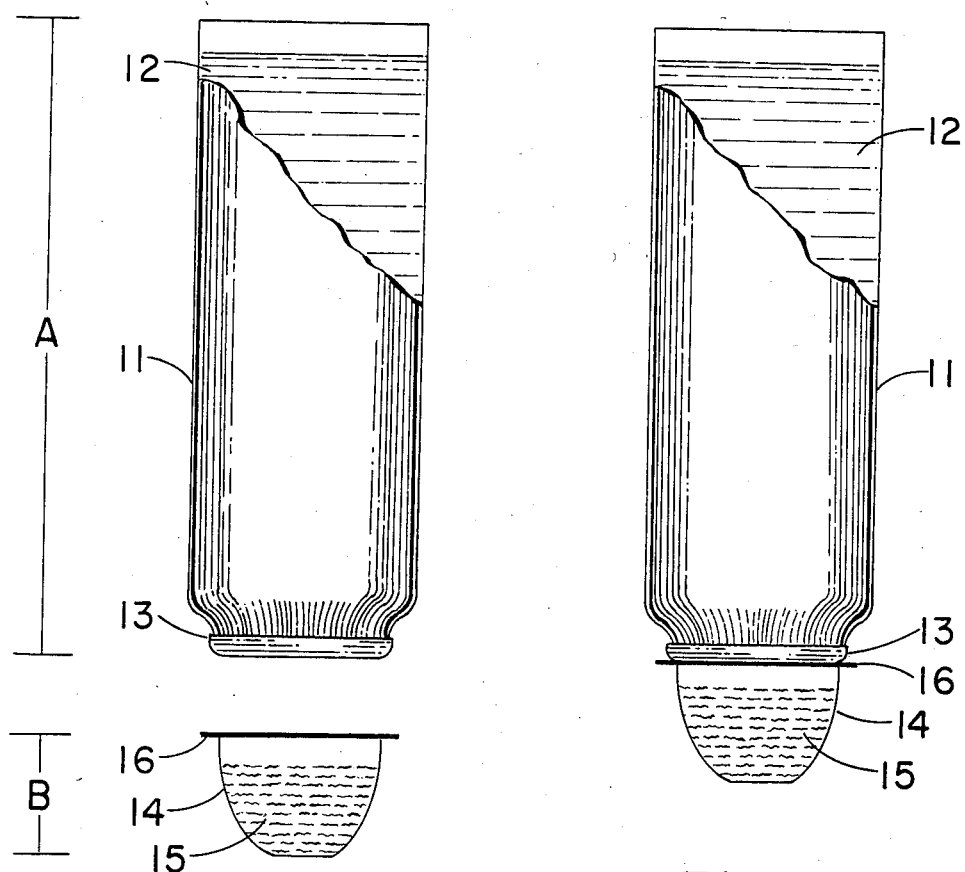

MEANS FOR CONSECUTIVE INTRODUCTION OF CO-ACTING STERILANTS INTO A STERILIZING CHAMBER

CROSS-REFERENCE TO RELATED APPLICATIONS

This application is a continuation-in-part of my copending application Ser. No. 492,709, filed May 9, 1983, which was, in turn, a continuation-in-part of application Ser. No. 212,973, filed Feb. 13, 1981. Both applications are now abandoned.

BACKGROUND OF THE INVENTION

1. Field of the Invention

This invention is in the field of devices for sterilization which involve the exposure of various objects to chemical vapors capable of co-acting to inactivate microorganisms. More specifically, the present invention is in the field of unitary devices for successive introduction of chemicals into a reaction space.

2. Description of the Prior Art

The germicidal activity of ethylene oxide was first described by Schrader and Bossert in 1936 in U.S. Pat. No. 2,037,439. One year later, in U.S. Pat. No. 2,075,845, Gross and Dixon presented detailed experimental evidence showing that for materials to be sterilized successfully, a critical minimal water content was required. In 1949, Kaye and Phillips, in American Journal of Hygiene, V. 50, pp. 296-306, showed that the relative humidity of the air in the sterilizing chamber was of critical importance in determining whether an object would be sterilized. The relative humidity was shown to affect the equilibrium moisture content of the goods being sterilized; these authors reported that there was an optimum desirable relative humidity (RH) which gave the most rapid sterilization, in the range between 20 and 70% RH. Since then, there have been hundreds of research and review papers published on the subject of the effect of water on ethylene oxide sterilization, and the notion of an optimum moisture level in the air and/or in the goods has been reconfirmed. During the same period, dozens of patents have been issued, and sterilizing apparatus manufactured, in which means of producing the desired relative humidity of the air or moisture content of the goods were detailed and provided. While the necessity for some moisture, but not too much, has been demonstrated unequivocally and a number of hypotheses have been advanced as to the reasons for this, there is still no clear-cut proof of the role of water in the inactivation of microorganisms. Nevertheless, it is an empirical fact in sterilization by means of ethylene oxide that the goods being treated cannot be dry and must not be too wet.

The first ethylene oxide sterilizer to acknowledge the need for water was the Ben Venue Sterilizer Mark VIII (1959) whose operating instructions specified that all instruments were to be washed and blotted dry prior to exposure. In the same year, the Wilmont-Castle Company introduced a gas sterilizer containing a glass water bottle, from which small amounts of water could be discharged, through a heated tube, into the chamber. By the next year, the American Sterilizer Company had introduced a similar device which was later followed by sterilizers which used piped-in steam to add the required moisture. In 1966, the 3M Company introduced a "portable" sterilizer into the chamber of which a wetted sponge was to be added to provide moisture.

Ethylene oxide processes played an increasingly important role in the commercial large-scale sterilization of sterile, disposable medical devices, and in such processes, it was found helpful to "precondition" all the cartons of packaged goods in a separate humidifying and heating chamber before transferring them to the large sterilizing chambers. Thereafter, live steam, as well as ethylene oxide gas, were injected into the sterilizing chamber.

Especially in the case of smaller sterilizing units, to which this invention most particularly refers, a number of difficulties and inconveniences occur with respect to the various ways of admitting water. The purpose of adding water is to achieve an RH of the air between 20 and 70%. This condition results in the absorption of amounts of moisture on the contaminated goods, sufficient to render the organisms susceptible to ethylene oxide, but not so great that the goods are saturated to an extent which makes the ethylene oxide too dilute to act effectively. Therefore, just the proper amount of water must be added to the sterilizing chamber.

Placing a wet sponge in the chamber adds an uncontrolled amount of water; the other systems detailed above are expensive, complicated, tend to clog, or depend upon the operator's accuracy for water addition. Sterilizers which admit live steam for humidification often contain RH sensors to regulate the steam entry. However, such sensors have been found to go completely awry when exposed a few times to ethylene oxide vapor. Because of this, a very expensive and complex instrument has been developed to permit the operator to analyze the concentrations of water and ethylene oxide vapors in the air.

In other attempts to address the problems discussed herein, McDonald, in U.S. Pat. No. 3,068,064, provides a bottle having sensing means therewithin to determine the amount of water contained in the bottle; water from the bottle is then conducted into the sterilizing chamber. However, McDonald provides no precise measurement of water or water vapor admitted into his sterilizing chamber; the quantity of water is dependent in part upon the volume contained in the bottle.

In U.S. Pat. No. 4,066,399, Gunther provides an aerosol container analogous to the bottle of McDonald, but provides no sensor to determine whether water is or is not present therein; in addition, Gunther uses a soluble organic component as part of his humidifying agent. Both McDonald and Gunther further require separate valves and controls for their water-addition systems.

It might seem obvious that if water vapor and ethylene oxide vapor are both required, and that since they are completely miscible one with the other, a mixture of the two chemicals might be made before admitting them to the chamber and the successive addition from separate containers would not be necessary. This, however, is not possible to accomplish, since ethylene oxide reacts with water to form ethylene glycol. The ethylene glycol thus formed reacts with further ethylene oxide to produce a glycol-ether compound. The reaction between the glycol and further ethylene oxide continues with the formation of high-molecular-weight polymers of ethylene oxide which are ineffective as sterilizing agents. The speed of these reactions depends upon a number of conditions, including the temperature and the presence of catalytic impurities, but the fact that they do take place means that ethylene oxide is not stable for long periods of time in the presence of water. Therefore, it is not possible to store an effective sterilizing mixture of ethylene oxide and water in a common container for any reasonable length of time.

While ethylene oxide and water react to form polymeric glycol ethers, this occurs generally only in the liquid phase, or where the concentration of each reactant is high enough to provide the building material necessary for the polymer. In the vapor phase, while the reaction is theoretically possible, the mass of monomer and the time of contact is negligible, and the production of polymer is so slight as not to be objectionable.

In the context of the foregoing discussion, "co-active liquids", as used herein, is defined to mean a plurality of liquids which would react with one another if mixed or stored together at the concentrations existing in separate containers, but which produce a desired sterilizing effect if sequentially vaporized into a sterilizing chamber.

It is therefore seen as difficult to devise a system for delivering both ethylene oxide vapor and water vapor in a practical manner to a sterilizing chamber without providing two separate receptacles to contain the ingredients, and appropriate valving and piping to conduct the components to the sterilizing chamber at the proper time.

SUMMARY OF THE INVENTION

The present invention provides for the sequential introduction of water and ethylene oxide measured out in the quantities required by the size of the sterilizing chamber and by the temperature at which it is to be operated, in at least two separate but contiguous containers fastened together in such a way that the first one is pierced by a piercing mechanism to release and evaporate its contents into the chamber; when the chamber conditions are appropriate as indicated by the pressure reached, elapsed time or other criteria, the second container is pierced by the same piercing mechanism.

BRIEF DESCRIPTION OF THE DRAWINGS

FIG. 1 is a partially cut-away side elevation of the components of the container of the present invention.

FIG. 2 is a side elevation of the assembled container of the present invention.

DESCRIPTION OF THE PREFERRED EMBODIMENTS

Figure 3:
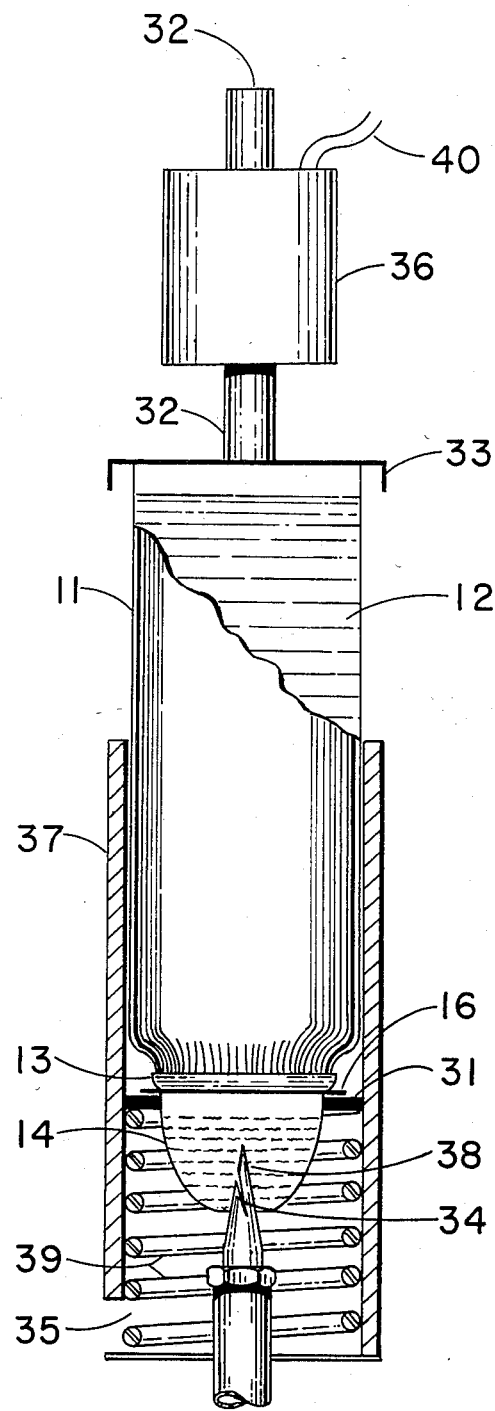
FIG. 3 is a side view, partly in section, of apparatus for holding and piercing the sealing means.

FIG. 1 shows the preferred embodiment of the present invention in a partially cut-away side elevation, showing first container 14 and second container 11. Containers 11 and 14 are each made of material which is inert to the contained fluid for the period of time during which storage is likely to be encountered. In FIG. 1, second container 11 is made of metal such as, e.g., aluminum, to satisfy the inertness requirement. The contents 12 are generally liquid under the conditions of interior storage pressure and ambient temperature.

Closing and sealing means 13 provides a closure for second container 11, and a site for holding second container 11 in apparatus 37, described with reference to FIG. 3 hereinbelow. Closure 13 can be affixed to second container 11 after it is formed, or the two can be integral. It is sufficient that the seal between closure 13 and second container 11 be vapor-tight; this seal can be achieved by providing matching threads on the two parts, with suitable gasket means therebetween, by adhering the parts, heat or electron-beam fusion, or other means known to those skilled in the art, which means form no part of this invention.

First container 14 is generally designed to contain water; the material from which first container 14 is formed, as is the case with second container 11, is necessarily one to which the contained chemical is inert, but which is further capable of being opened or punctured by piercing means described hereinbelow. First container 14 is shown here as being substantially transparent, having disposed therewithin a second chemical 15. Such transparency is a matter of convenience only, and is not critical to the efficacy of the invention.

Closure and sealing means 16 provides a closure for container 14, and a site for holding the compound container in apparatus 37. Sealing means 16 is optionally integral with sealing means 13; in different terms, container 14 can be provided without sealing means, being sealed by affixing it in sealing juxtaposition to container 11. This latter step can be achieved in a number of ways well known to those skilled in the art, and as such forms no part of this invention. Such sealing can be achieved, for instance, by forming containers 11 and 14 of the same piece of material, with a membrane therebetween serving as both sealing means 13 and 16, and thereafter filling the containers from the opposing ends and sealing them; alternatively, means 13 and 16 can be provided with matching threads, to permit their assembly after filling and sealing container 11, and filling container 14; or the seal for placement can be on container 14, with a concommitant order of filling and sealing.

FIG. 2 shows contiguous containers 11 and 14 assembled into a unitary structure for placement into the apparatus 37, described with reference to FIG. 3, for holding the containers, and for piercing sealing means 13 and 16.

FIG. 3 shows containers 11 and 14 assembled and disposed within apparatus 37 for holding the containers and piercing the sealing means 13 and 16. Piercing means 38 is a pointed device capable of piercing the material of which the containers are formed, and optionally is provided with a slot or interior hole to permit the liquid within the containers to pass through, as well as around, the tip of the piercing means into the space in which the sterilization or chemical treatment occurs. Collar 31 provides means on which to dispose the assembled containers; spring 39 permits the containers to be ejected after use.

Figure 4:
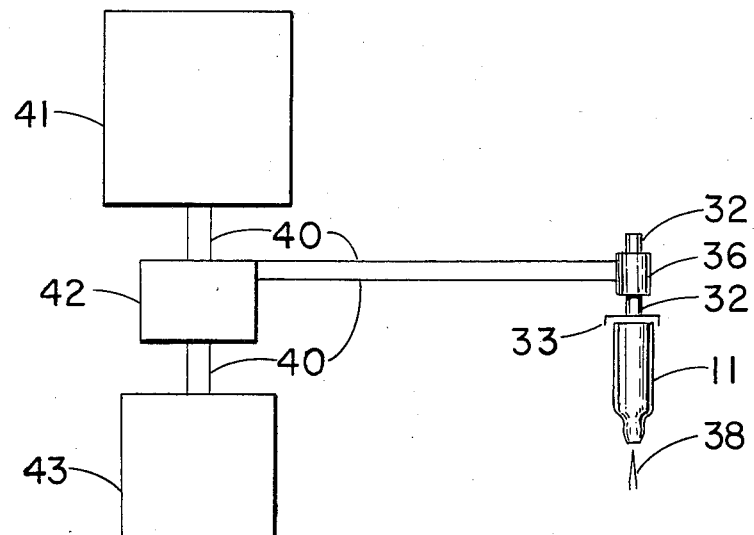
FIG. 4 is a simplified schematic diagram of interval-maintenance means.

Positioning means 33 provides the means to urge containers 11 and 14 toward piercing means 38 after second container 14 has been pierced by the action of piercing means 38; the order and manner of operation are set forth hereinbelow in connection with the description of the circuit diagram in FIG. 4. After either or both seals are pierced, the liquid or vapor runs or diffuses into the working space through slot or hole 34 in piercing means 38, and through drain passage 35 in apparatus 37.

Positioning means 33 is shown disposed on shaft 32 which is in turn carried within motive means 36 to urge means 33, and in turn the unitary structure comprising a plurality of containers 11 and 14, onto piercing means 38. Motive means 36 can be a number of means known to those skilled in the art, such as, e.g., a solenoid or an electric or mechanical drive means, and as such forms no part of the present invention. In similar fashion, operation of piercing means 38 can be effected by means well known to those skilled in the art, and such means do not form a part of this invention; any means 36 such as set forth above can be used to provide motion to positioning means 33, which in turn causes means 38 to pierce first container 11. While positioning means 33 is shown above container 11 in FIG. 3, those skilled in the art will realize that it could as well be placed below piercing means 38, and serve to drive that device. It is sufficient that means 38 be capable of moving far enough with respect to container 11 to pierce sealing means 13.

In the operation of the present invention, a medical instrument to be sterilized is placed within an enclosure to be treated with ethylene oxide. Containers 11 and 14, assembled and having their contents therewithin, are placed as shown in apparatus 37. The sterilizing device is closed and evacuated as described in my U.S. Pat. Nos. 4,337,223 and 4,410,492, both assigned to the same assignee as the present invention. Piercing means 38 is activated to open first container 14, allowing a measured amount of water to flow into the evacuated chamber.

The water evaporates under the reduced pressure in the chamber, and affords between about 20 and 70%, and preferably about 50%, RH in the chamber. As noted hereinabove, the provision of a humid environment is necessary to secure optimum sterilizing efficacy from the ethylene oxide.

After a time lapse of about four minutes, but in any event sufficient to permit substantially complete vaporization of the water, second container 11 is opened by the action of piercing means 38. The vapor pressure of the ethylene oxide contained therewithin is more than adequate to cause container 11 to empty completely into the sterilizing chamber. With the water present in the vapor phase, however, the objectionable problem of polymerization of the ethylene oxide referred to hereinabove is obviated.

Figure 5:
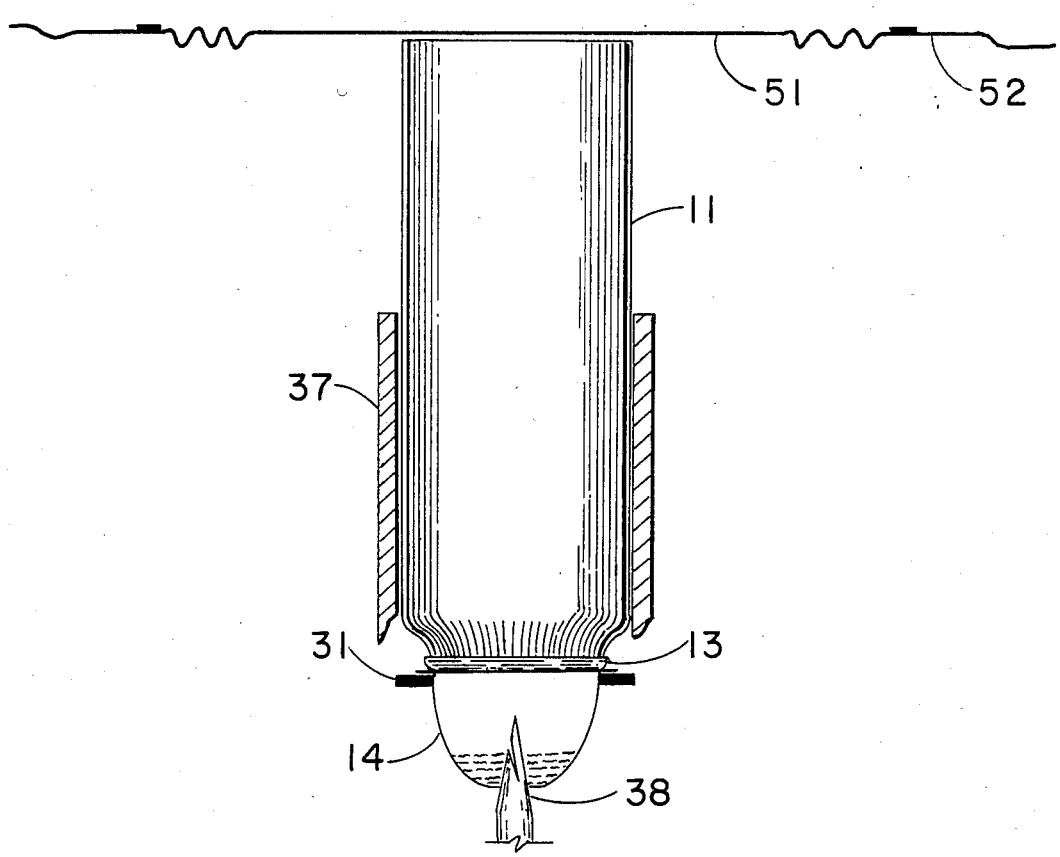
FIG. 5 is an elevation of a device showing an alternative method of opening a container.

Maintaining a vaporization time interval after opening the first container prior to opening the second container is necessary for optimum sterilization efficiency in the chamber. As noted hereinabove, a time lapse of about four minutes is generally adequate to permit effective vaporization of the water, and a timer could be used to effect the necessary humidity within the sterilizing chamber. Alternatively, a device for determining RH within the chamber could be used to determine the appropriate time for opening second container 14. In any event, such means are a necessary part of the device; FIG. 4 is a simplified schematic diagram showing such means. Means 41 is a pressure, RH, timer or other device; on the occurrence of the appropriate time, humidity, pressure or other event, means 41 energizes relay 42, causing second container 11 to be urged onto piercing means 38. Power source 43 is preferably electrical, but can be any appropriate energy source. Lines 40 transmit the necessary energy, i.e., electrical or fluid, to motive means 36. In FIG. 5, there is shown an alternate embodiment of the present invention, where the cover or lid 52 of the sterilizing apparatus contains a diaphragm 51. Contiguously joined containers 11 and 14 are positioned in holder 37. After first container 14 has been pierced, the operation of diaphragm 51 causes second container 11 to be urged onto piercing means 38, thereby permitting the ethylene oxide within second container 11 to vaporize into the sterilizing chamber.

Further reference to the operation of the present invention is found at Col. 3, lines 38 through 46, of my U.S. Pat. No. 4,410,492, issued Oct. 18, 1983, and assigned to the same assignee as the invention described and claimed herein. The sterilizing chamber is shown as reference character 10 in U.S. Pat. No. 4,410,492; in that patent, valve 14 is initially adjusted to permit a vacuum to be drawn on both sides of diaphragm 51 shown in FIG. 5 herein. Upon the attainment of sufficient vacuum with the sterilizing chamber, valve 14 in U.S. Pat. No. 4,410,492 is adjusted to permit external pressure to bear upon diaphragm 51, causing it to urge container 11 onto piercing means 38 as noted above.

The material in second container 11 can be either undiluted ethylene oxide, or can be that sterilant admixed with any of a number of chemically and physiologically inert diluents such as, e.g., dichlorodifluoromethane, trichlorotrifluoroethane and the like, halocarbons with boiling points close to that of ethylene oxide being preferred. Such admixtures can be made with a single inert diluent or a plurality thereof.

Upon circulation and recirculation of the ethylene oxide and humid atmosphere as described in U.S. Pat. Nos. 4,337,223 and 4,410,492, highly efficient and substantially complete inactivation of microbial contaminants is effected.

Those skilled in the art will realize that the arrangement of the apparatus of the present invention prevents premature release of the second component into the space to be treated until the first component has been properly disposed. In the case of sterilization with ethylene oxide, there is neither a chance of water soaking into materials to be treated and thus creating too high a localized humidity, nor of the water evaporating prematurely or being withdrawn from the chamber before the effective concentration of the ethylene oxide is established. By the cooperation among the elements, the device eliminates intervening valves, pipes and controls, and provides a fail-safe and effective means of sequential disposition of chosen materials within a working space.

Modifications, changes and improvements to the preferred forms of the invention herein disclosed, described and illustrated may occur to those skilled in the art who come to understand the principles and precepts thereof. Accordingly, the scope of the patent to be issued herein should not be limited to the particular embodiments of the invention is set forth herein, but rather should be limited only by the advance of which the invention has promoted the art.

I claim:

1. A unitary device having a plurality of chambers for the sequential addition of a plurality of co-reactive liquids to a sterilizing apparatus, a first liquid comprising water in a sealed first container, said first container being contiguous with a sealed second container having therewithin a second liquid comprising at least ethylene oxide, a holder for said containers, means for opening said containers sequentially, and means for maintaining a vaporization-time interval after opening said first container prior to opening said second container.

2. The device of claim 1 wherein said liquid in said second container is a mixture of ethylene oxide and at least one chemically and physiologically inert diluent.

3. The device of claim 2 wherein said inert diluent is at least one halocarbon.

4. The device of claim 2 wherein said inert diluent is dichlorodifluoromethane.

* * * * *